United States Patent
De The et al.

(10) Patent No.: US 11,077,139 B2
(45) Date of Patent: Aug. 3, 2021

(54) COMBINATION OF AN ARSENIC COMPOUND AND AT LEAST ONE RETINOID FOR TREATING ACUTE MYELOID LEUKEMIA

(71) Applicants: INSERM (Institut National de la Sante et de la Recherche Medicale), Paris (FR); Universite Paris Diderot—Paris 7, Paris (FR); Centre National de la Recherche Scientifique (CNRS), Paris (FR); Universita di Perugia, Perugia (IT); American University of Beirut, Beirut (LB); Assistance Publique-Hopitaux de Paris (APHP), Paris (FR)

(72) Inventors: Hugues De The, Paris (FR); Ali Bazarbachi, Beirut (LB); Hiba El Hajj, Beirut (LB); Maria Paula Martelli, Perugia (IT); Brunangelo Falini, Perugia (IT)

(73) Assignees: INSERM (INSTITUT NATIONAL DE LA SANTE ET DE LA RECHERCHE MEDICALE), Paris (FR); UNIVERSITE PARIS DIDEROT—PARIS 7, Paris (FR); CENTRE NATIONAL DE LA RECHERCHE SCIENTIFIQUE (CNRS), Paris (FR); UNIVERSITA DI PERUGIA, Perguia (IT); AMERICAN UNIVERSITY OF BEIRUT, Beirut (LB); ASSISTANCE PUBLIQUE-HOPITAUX DE PARIS (APHP), Paris (FR)

(*) Notice: Subject to any disclaimer, the term of this patent is extended or adjusted under 35 U.S.C. 154(b) by 205 days.

(21) Appl. No.: 15/107,749

(22) PCT Filed: Dec. 30, 2014

(86) PCT No.: PCT/EP2014/079422
§ 371 (c)(1),
(2) Date: Jun. 23, 2016

(87) PCT Pub. No.: WO2015/101618
PCT Pub. Date: Jul. 9, 2015

(65) Prior Publication Data
US 2016/0317579 A1    Nov. 3, 2016

(30) Foreign Application Priority Data
Dec. 30, 2013    (EP) .................................. 13306891

(51) Int. Cl.
  *A61K 33/36*    (2006.01)
  *A61K 31/203*    (2006.01)
  *A61K 31/555*    (2006.01)

(52) U.S. Cl.
  CPC ........... *A61K 33/36* (2013.01); *A61K 31/203* (2013.01); *A61K 31/555* (2013.01)

(58) Field of Classification Search
None
See application file for complete search history.

(56) References Cited

FOREIGN PATENT DOCUMENTS

| EP | 2 005 954 A2 | 12/2008 |
|---|---|---|
| WO | 99/24029 A1 | 5/1999 |
| WO | 2013/059320 A1 | 4/2013 |

OTHER PUBLICATIONS

Hu (PNAS, Mar. 3, 2009, vol. 106, No. 9, pp. 3342-3347).*

(Continued)

*Primary Examiner* — Nicole P Babson
*Assistant Examiner* — Lori K Mattison
(74) *Attorney, Agent, or Firm* — W&C IP

(57) ABSTRACT

The present invention relates to methods and pharmaceutical compositions for the treatment of acute myeloid leukemia. In particular, the present invention relates to a method for treating NPM-1-driven acute myeloid leukemia (AML) in a subject in need thereof comprising administering the subject with a therapeutically effective amount of at least one (Continued)

Figure 1A:
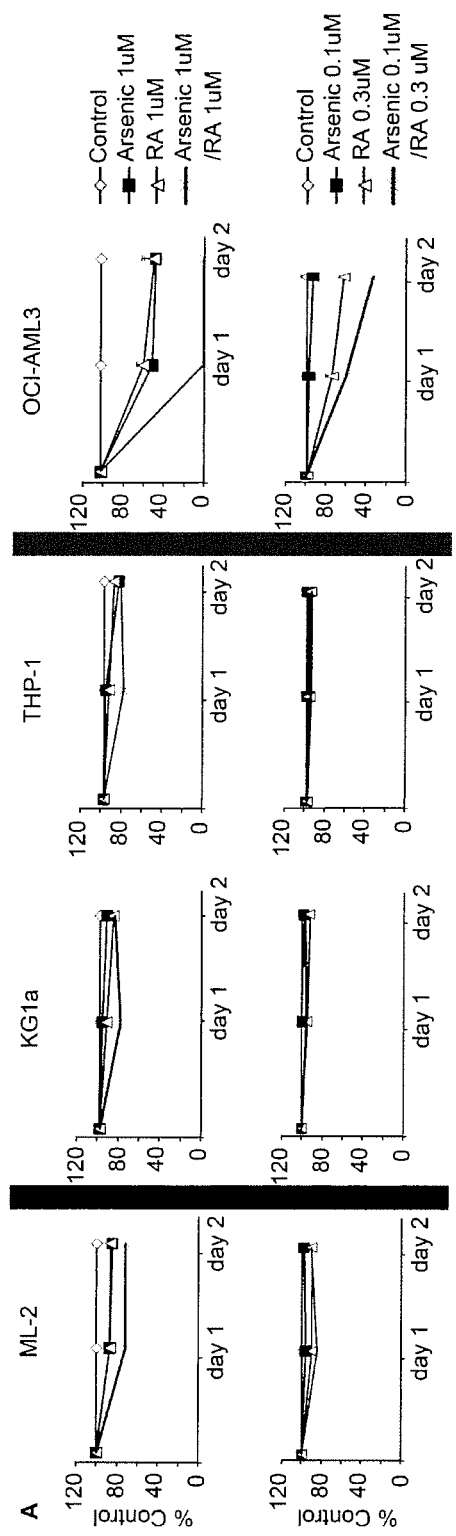

arsenic compound and with a therapeutically effective amount of at least one retinoid.

4 Claims, 6 Drawing Sheets

(56) References Cited

OTHER PUBLICATIONS

Grimwade (Acute promyelocytic leukemia: a paradigm for differentiation therapy. In: Acute Myelogenous Leukemia 2009 (pp. 219-235) Springer New York).*
Kutny (Blood 2010 116:3305).*
Schlenk (haematologica | 2009; 94(1), pp. 54-60).*
Roboz (CANCER Nov. 1, 2008 / vol. 113/ No. 9, p. 2504-2511).*
https://www.cancerresearchuk.org/about-cancer/cancer-in-general/treatment/cancer-drugs/drugs/arsenic, accessed Jul. 10, 2018.*
http://chemocare.com/chemotherapy/drug-info/atra.aspx, accessed Jul. 10, 2018.*
Burnett (CANCER Mar. 15, 2007 / vol. 109 / No. 6, p. 1114-1124).*
Yague, The Journal of Biological Chemistry 278, 10344-10352, Mar. 21, 2003.*
MD Anderson (Blood, vol. 93, No. 8 Apr. 15, 1999: pp. 2478-2484).*
Kutny (Blood (2010) 116 (21): 3305).*
Martelli (Blood (2007) 110 (11): 868).*
Stanford (https://clinicaltrials.gov/ct2/show/NCT01835288, 4/48/2013).*
Shen. PNAS, vol. 101, No. 15, 2004. p. 5328-5335.*
Lin et al.; "Synergistic effect of all-trans-retinoic acid and arsenic trioxide on growth inhibition and apoptosis in human hepatoma, breast cancer, and lung cancer cells in vitro"; World Journal of Gastroenterology, vol. 11, No. 36, Sep. 28, 2005; pp. 5633-5637.
Falini et al.; "Acuter myeloid leukemia with mutated nucleophosmin (NPM1): Any hope for a targeted therapy?"; Blood Reviews, vol. 25, No. 6, Jan. 1, 2011, pp. 247-254.
Schlenk et al.; "Gene mutations and response to treatment with all-trans retinoic acid in elderly patients with acute myeloid leukemia. Results from the AMLSG Trial AML HD98B"; Haematologica—The Hematology Journal, vol. 94, No. 1, Jan. 2009, pp. 54-60.

* cited by examiner

| | Blasts in Bone Marrow (%) | | |
|---|---|---|---|
| | Day 0 | Day 15 | After stopping |
| Patient 4 | 20% | 5% | 33% |
| Patient 5 | 27% | 3% | 9% |
| Patient 6 | 55% | 14% | 79% |

Patient 4

| Days | d1 | d8 | d15 | d23 | d28 | d35 | d39 | d46 | d48 | d63 |
|---|---|---|---|---|---|---|---|---|---|---|
| RA | | | | | | | | | | |
| Arsenic | | | | | | | | | | |
| Blasts in BM (%) | 15 | 20 | 38 | 5 | | | 6 | | | 33 |

COMBINATION OF AN ARSENIC COMPOUND AND AT LEAST ONE RETINOID FOR TREATING ACUTE MYELOID LEUKEMIA

FIELD OF THE INVENTION

The present invention relates to methods and pharmaceutical compositions for the treatment of acute myeloid leukemia.

BACKGROUND OF THE INVENTION

Acute myeloid leukemia (AML) is a genetically heterogeneous disease, with a highly variable prognosis and an overall high mortality rate. The 5-year overall survival of adult AML patients is less than 50%, and only 20% of elderly patients survive over 2 years (1). Cytogenetic alterations classify AML into three risk based-categories: favorable, intermediate and unfavorable (2). Patients with normal karyotype belong to the intermediate risk category and their prognosis is determined by specific genetic alterations, particularly Nucleophosmin-1 (NPM-1) mutation and FMS-like tyrosine kinase-3 (FLT-3) internal tandem duplication (ITD) (3).

NPM-1 is an essential gene (4) encoding a nucleolar shuttling protein (5), with multiple functions, including stabilization of the $p14^{Arf}$ tumor suppressor protein, regulation of ribosome biogenesis, control of centrosome duplication and P53 activation (4-5). In mutant NPM-1, critical tryptophan residues in the C-terminus are lost and a de novo nuclear export signal is created. This leads to accumulation of mutant NPM-1 in the cytoplasm of leukemic cells, rather than in the nucleolus, together with normal NPM-1. NPM-1 mutations drive leukemogenesis, as hematopoietic disorders were observed in transgenics or knock-in mice (6-11).

Some studies suggested that addition of retinoic acid (RA) to conventional chemotherapy improves survival, selectively in AML patients harboring the NPM-1 mutation but not FLT3-ITD (12). Arsenic trioxide (arsenic) and RA are very effective treatments for acute promyelocytic leukemia (APL), a distinct AML subtype characterized by the expression of the promyelocytic leukemia/RA receptor alpha (PML/RARA) fusion protein (13-14). PML/RARA delocalizes PML, a protein implicated in control of P53-driven senescence, and PML nuclear bodies (NB) are implicated in both APL pathogenesis and therapy response (15). Both RA and arsenic induce degradation of PML/RARA, and their combination definitively cures APL in mice (15-17) and patients (18-20). Yet, in NPM-1 mutant AMLs, the basis for the proposed clinical response to RA remains obscure.

SUMMARY OF THE INVENTION

The present invention relates to methods and pharmaceutical compositions for the treatment of acute myeloid leukemia. In particular, the present invention is defined by the claims.

DETAILED DESCRIPTION OF THE INVENTION

Nucleophosmin-1 (NPM-1) is the most frequently mutated gene in acute myeloid leukemia (AML). Addition of retinoic acid (RA) to chemotherapy was proposed to improve survival of these patients. Here, the inventors observed that in AML cell lines or primary samples, RA or arsenic trioxide induce proteasomal degradation of mutant NPM-1, leading to apoptosis. NPM-1 mutation delocalizes NPM-1 from the nucleolus, but also disorganizes promyelocytic leukemia (PML) nuclear bodies. Combined RA/arsenic treatment significantly reduced bone marrow blasts in three patients and corrected the sub-nuclear localization of both NPM-1 and PML. These findings, highly reminiscent of acute promyelocytic leukemia therapy, could explain the proposed benefit of adding RA to chemotherapy in NPM-1 mutant AMLs, and warrant a broader clinical evaluation of the RA/arsenic combination.

Accordingly a first aspect of the invention relates to a method for treating NPM-1-driven acute myeloid leukemia (AML) in a subject in need thereof comprising administering the subject with a therapeutically effective amount of at least one arsenic compound and with a therapeutically effective amount of at least one retinoid.

As used herein the term "NPM-1" has its general meaning in the art and refers to nucleophosmin-1 (which may also be referred to as also known as NO38, nucleolar phosphoprotein B23, numatrin, or NPM-1). As used herein the term "NPM-1 mutation" refers to any mutation that could occur in NPM-1 and that is associated with AML progression. The mutations are present in the coding regions. Any NPM-1 mutation is encompassed by the invention, including point mutations, inversion, translocations, deletions, frame shifts . . . . Exemplary mutations are described in the literature (e.g. B. Falini, C. Mecucci, E. Tiacci, M. Alcalay, R. Rosati, L. Pasqualucci et al. Cytoplasmic nucleophosmin in acute myelogenous leukemia with a normal karyotype N Engl J Med, 352 (2005), pp. 254-266) and are encompassed in the invention. Mutations in NPM-1 may be identified by any suitable method in the art, but in certain embodiments the mutations are identified by one or more of polymerase chain reaction, sequencing, histochemical stain for NPM-1 localization, as well as immunostaining method using anti-mutant-NPM-1 antibody.

In its broadest meaning, the term "treating" or "treatment" refers to reversing, alleviating, inhibiting the progress of, or preventing the disorder or condition to which such term applies, or one or more symptoms of such disorder or condition. In particular, the method of the present invention is particularly suitable for inducing growth arrest of AML cells with mutant NPM-1, reducing bone marrow blasts in NPM-1 mutant AML patients and/or correcting the defects in nucleolar organization and function imposed by NPM-1 mutation.

As used herein, the term "arsenic compound" is intended to include arsenic and any compound having the same biological properties as arsenic. The expression "compound having the same biological properties as arsenic" is understood to mean any compound which, like arsenic, is an inhibitor of phosphatase and/or is capable of creating covalent adducts by binding with dithiol groups.

In some embodiments, the arsenic compound is selected from the group consisting of arsenic, arsenic trioxide ($As_2O_3$), arsenic hexoxide ($As_4O_6$), melarsoprol and arsenic sulfur derivative.

As used herein the term "retinoid" refers to a class of vitamin A derivatives consisting of four isoprenoid units joined in a head-to-tail manner. Examples of retinoids useful in the present process include retinoic acid (RA), all-trans retinoic acid (ATRA), 9-cis-retinoic acid, 13-cis-retinoic acid, 9,13-di-cis-retinoic acid, benzoic acid-terminated retinoids and their heterocyclic analogs such as TTNPB, TTAB, AM80, AM580, SRI 1251, SRI 1247, CD666, CD367, chalcone-4-carboxylic acids, flavone-4'-carboxylic acids, etc. (Loeliger et al., 1980, Eur. J. Med. Chem-Dhim. Ther. 15:9), (Kagechika et al, 1989, J. Med. Chem. 32:834), (Dawson, et al. 1995, J. Med. Chem. 38:3368) as well as napthalenecarboxylic acid-terminatedated retinoids such as TTNN, CD437, CD417 or adapalene (Dawson et al., 1983, J. Med. Chem. 26:1653), (Dhar et al., 1999, J. Med. Chem. 42:3602) and many other carboxylic acid retinoids (AGN 190299 or tazarotenic acid and RQ 10-9359 or acitretin). Some retinoids are illustrated below:
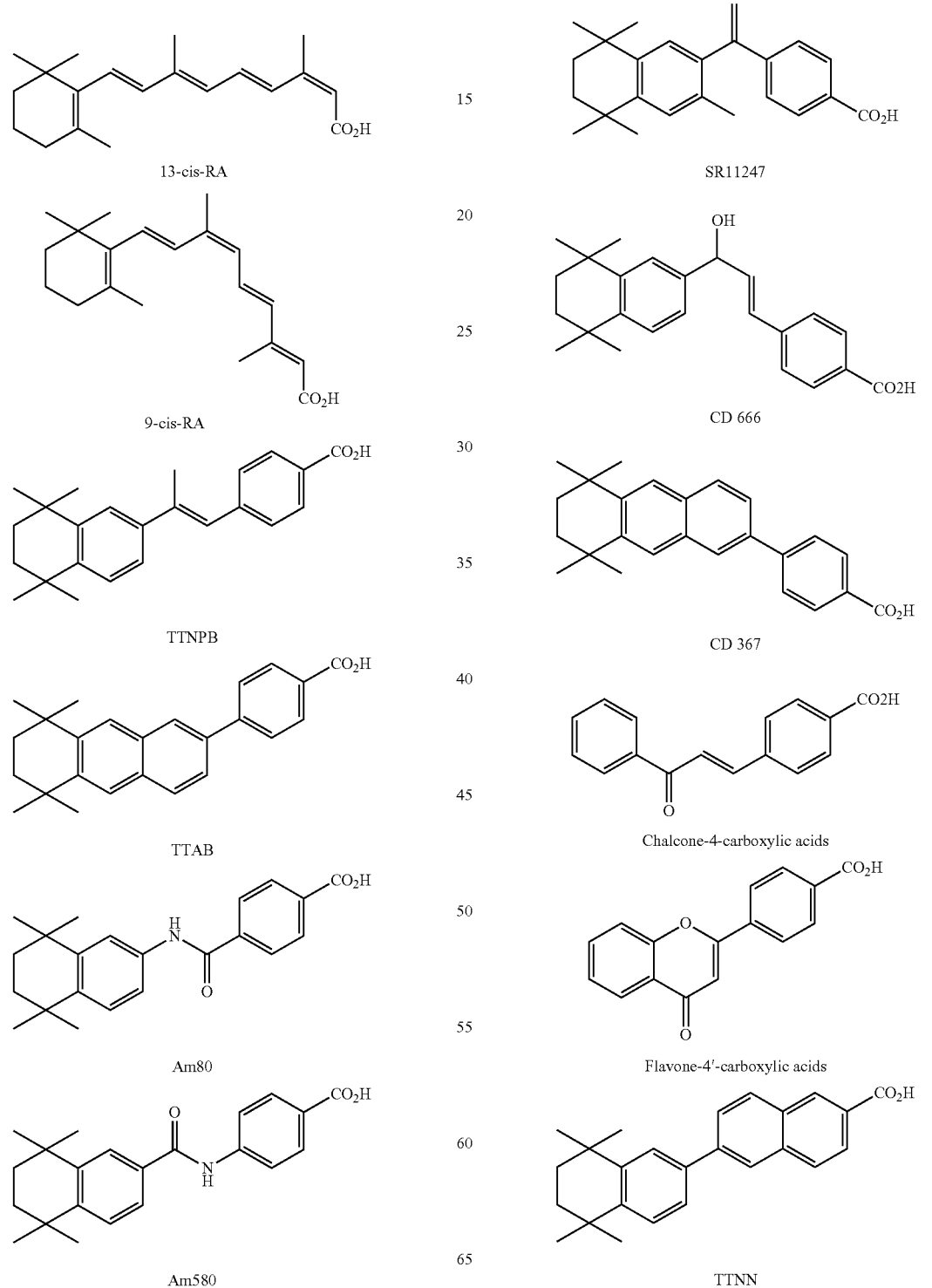

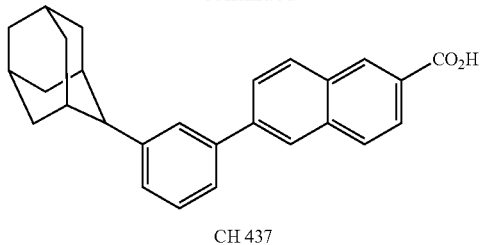

CH 437

Additional synthetic retinoids useful in the present method are described and illustrated below as well as in Dawson et al, "Synthetic Retinoids and their Usefulness In Biology and Medicine," Vitamin A and Retinoids, M. A. Livrea (ed.), pp, 161-196 (2000). See also: retinoids listed in http://www.chem.qmul.ac.uk/iupac/misc/ret.html as well as in Arch. Biochem. Biophys., 1983, 224, 728-731; Eur. J. Biochem., 1982, 129, 1-5; J. Biol. Chem., 1983, 258, 5329-5333; Pure Appl. Chem., 1983, 55, 721-726; Biochemical Nomenclature and Related Documents, 2nd edition, Portland Press, 1992, pages 247-251.

By a "therapeutically effective amount" is meant a sufficient amount of the actives ingredients of the invention to treat AML at a reasonable benefit/risk ratio applicable to any medical treatment. It will be understood that the total daily usage of the active ingredients of the invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific active ingredients employed; the duration of the treatment; drugs used in combination or coincidental with the specific active ingredients employed; and like factors well known in the medical arts. For example, it is well within the skill of the art to start doses of the active ingredients at levels lower than those required to achieve the desired therapeutic effect and to gradually increase the dosage until the desired effect is achieved.

Typically, the arsenic compound is administered by intravenous route or oral route (e.g. for arsenic sulfur derivative) and the retinoid is administered by the oral route.

According to the invention, the active ingredients of the invention may be administered as a combined preparation for simultaneous, separate or sequential use in the treatment of AML.

The active ingredients of the invention may be combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Typically, the carrier is a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

The present invention also relates to a combination of at least one arsenic compound with at least one retinoid for use in the treatment of NPM-1-driven acute myeloid leukemia (AML) in a subject in need thereof.

The present invention also relates to a kit-of-parts comprising at least one arsenic compound and at least one retinoid for use in the treatment of NPM-1-driven acute myeloid leukemia (AML) in a subject in need thereof.

The invention will be further illustrated by the following figures and examples. However, these examples and figures should not be interpreted in any way as limiting the scope of the present invention.

FIGURES

FIG. 1: RA and arsenic induce growth inhibition and apoptosis in NPM-1 mutated AML. A) AML cell lines with normal NPM-1 (ML-2, KG1a and THP-1) or mutated NPM-1 (OCI-AML3) were treated with arsenic (1 µM or 0.1 µM), RA (1 µM or 0.3 µM) or a combination of both. Cell growth (% of control) was assayed in triplicate wells. The results represent the average of at least three independent experiments. B) Annexin V staining of THP-1 or OCI-AML3 cells treated for 48 h as described. C) TUNEL assay of THP-1 or OCI-AML3 cells treated for 48 h as described. The results are the average of three independent experiments. D) Primary AML cells from three different AML patients were treated with arsenic (1 µM), RA (1 µM) or a combination of both. Cell growth (% of control) was assayed in duplicate wells. E) Percent of BM blasts in three NPM-1 mutated AML patients treated as indicated. F) Percent of blasts in weekly BM aspirates from a NPM-1 mutated AML patient treated with RA and arsenic. Treatment schedule is indicated.

FIG. 2: RA and arsenic induce proteasomal degradation of mutant NPM-1, and restore NPM-1 nucleolar localization. Western blot analysis for NPM-1, mutated NPM-1, actin or GAPDH in THP-1 and OCI-AML3 cells (A, C), and for NPM-1 and GAPDH in primary leukemic cells derived from AML patients (B). A representative of three independent experiments is shown. D) Growth (% of control) of OCI-AML3 and THP-1 cells treated with arsenic (1 µM), RA (1 µM), PS-341 (10 nM) either alone or in combination, for up to 48 h. Cell growth (% of control) was assayed in triplicate wells. The results depict one representative experiment among three independent ones. E) NPM-1 profile after treatment with RA/arsenic for 48 h. Graphs show quantification of nucleolar NPM-1 as averages of one Z-section/cell from 30 different cells of three independent experiments. Significant p-values are indicated by asterisks.

FIG. 3: Combination of RA and arsenic restores PML and SUMO-1 nuclear body formation. A) Primary leukemic blasts from one NPM-1 mutated AML patient on days 0 and 8 following in vivo treatment with RA/arsenic. NPM-1 was stained with anti-NPM-1 antibody (green), PML was stained with anti-PML antibody (red) and nuclei were stained with DAPI (blue). Higher magnification is shown in the right panel. (B-C) THP-1 cells (left panels) and OCI-AML3 cells (right panels) treated with RA/arsenic for up to 48 hr. (B) Same as A) in untreated OCI-AML3 cells. (C) Treatment of OCI-AML3 cells with RA/arsenic leads to SUMO-1 nuclear body formation. The results (B-C) depict one representative of three independent experiments. Graphs show quantification of PML and SUMO-1 NBs, as averages of one Z-section/cell from 30 different cells. Significant p-values are indicated by asterisks.

EXAMPLE

Material & Methods:

Patients, Cells and Treatments

KG1a, ML-2 and THP-1 AML cell lines (gift from F. Mazurier) with wt NPM-1, were grown in RPMI-1640 medium containing 10% fetal bovine serum (FBS) and antibiotics. OCI-AML3 AML cells (gift from D. Bouscary) harboring the NPM-1 mutation without FLT3-ITD were grown in MEM containing 20% FBS and antibiotics. Cells were seeded at a density of $2 \times 10^5$/ml. Primary AML cells (from either peripheral blood or BM) were extracted following ficoll separation and cultured in MEM-α supplemented with 20% FBS and antibiotics. These samples were collected after approval by the Institutional Review Board and after patients provided informed consent in accordance with the Declaration of Helsinki. Arsenic was used at 0.1 or 1 μM, RA at 0.3 or 1 μM, and the proteasome inhibitor PS-341, at 10 nM. Cell growth was assessed using the CellTiter 96® cell proliferation assay kit (Promega Corp., Madison, Wis., USA) or by trypan blue dye assay. Elderly AML patients with NPM-1 mutation that were judged unfit for chemotherapy, received compassionate RA (Vesanoid®, ROCHE) (45 mg/m²/day PO) and arsenic trioxide (Trisenox®, TEVA), intravenously (0.1 mg/kg/day).

FACS Analysis

Annexin V staining: Phosphatidyl-serine (PS) exposure in treated AML cells was assessed using Annexin V-FITC (Sigma). TUNEL assay: fluorescein-conjugated dUTP incorporated in nucleotide polymers was detected and quantified using flow cytometry. For both Annexin and TUNEL assays, approximately 10000 cells per sample were acquired and analyzed using CellQuest software.

Immunoblot Analysis

Cells were solubilized at 4° C. in lysis buffer. 50 μg of proteins were loaded onto a 12% SDS-polyacrylamide gel, subjected to electrophoresis, and transferred onto nitrocellulose membranes. Blots were incubated with specific antibodies, washed and proteins were visualized using the ECL chemiluminescence system (Santa Cruz, Germany). The following antibodies were used; monoclonal anti-wt NPM-1 (Abnova, Abcam), polyclonal anti-mutated NPM-1 (Abnova), anti-actin (Santa-cruz, Germany) and anti-GAPDH (Abnova).

Immunofluorescence and Confocal Microscopy

OCI-AML3 and THP-1 cells were cytospun onto glass slides (5 min, 800 rpm) and fixed with methanol at −20° C. Immunofluorescence assays were performed using anti-NPM-1, anti-SUMO1, or anti-PML primary antibodies. Images were acquired by confocal microscopy using a Zeiss LSM 710 confocal microscope (Zeiss, Oberkochen, Germany) with a Plan Apochromat 63/1.4 numeric aperture oil-immersion objective, using Zen 2009 (Carl Zeiss).

Synergy Studies and Statistical Analysis

Proliferation experiments on cell lines were repeated at least three times. Data are reported as the mean+/−standard error. Computerized combination index (CI) was generated automatically using CompuSyn software based on the CI-isobol method of Chou-Talalay et al., 2010. CI was used to assess synergistic effects (CI<1), additive effects (CI=1) or antagonistic effects (CI>1). Two statistical tests were performed to validate significance: the t-test and the one-way analysis of variance (ANOVA) test. *,  and * indicate p values≤0.05; 0.01 and 0.001, respectively. p-values less than 0.05 were considered significant.

Results:

RA/Arsenic Combination Induce Apoptosis in NPM-1 Mutated AML Cells

Figure 1B:
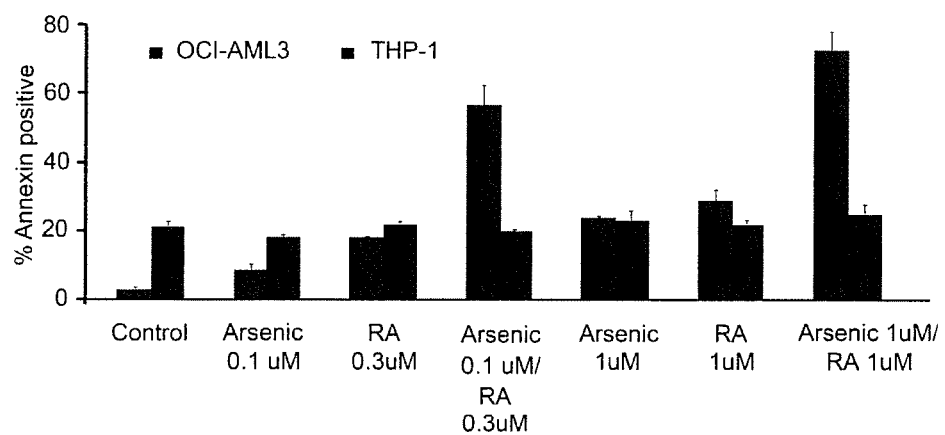
Figure 1C:
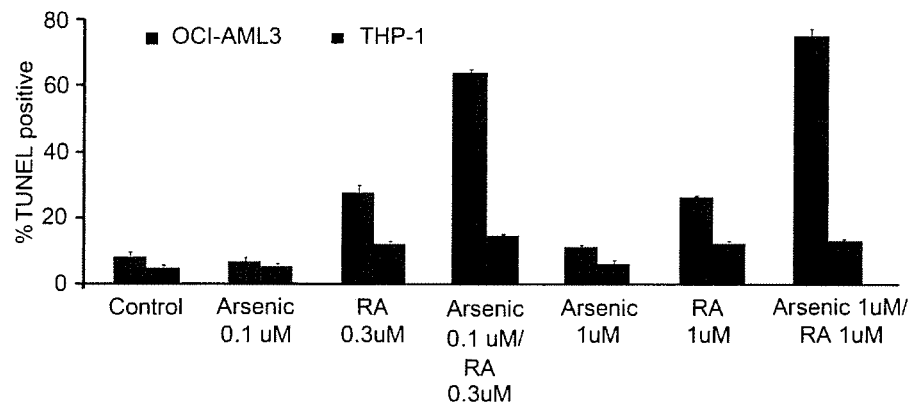

AML cell lines with mutated NPM-1 (OCI-AML3) or wild type (wt) NPM-1 (KG1a, ML-2, THP-1) were treated with RA and/or arsenic up to 48 h. OCI-AML3 cells were much more sensitive to RA than KG1a, ML-2 and THP-1 cells for growth suppression and/or cell death (FIG. 1A). OCI-AML3 cells were also considerably more sensitive to arsenic than control cells (FIG. 1A). Synergy studies, analyzed using a computerized combination index (CI) (21), revealed a strong synergistic effect of arsenic and RA for growth arrest in OCI-AML3 cells at 24 h (CI=0.46 and 0.035, for low or high arsenic concentration respectively) (FIG. 1A). Similarly, an increase in Annexin-V and TUNEL positivity was only observed in OCI-AML3 cells treated with arsenic or RA. Thus, this combination synergized for induction of apoptosis, reaching 75% after 48 h of treatment, exclusively in OCI-AML3 cells (FIGS. 1B and 1C).

Figures 1D, 1E, 1F:
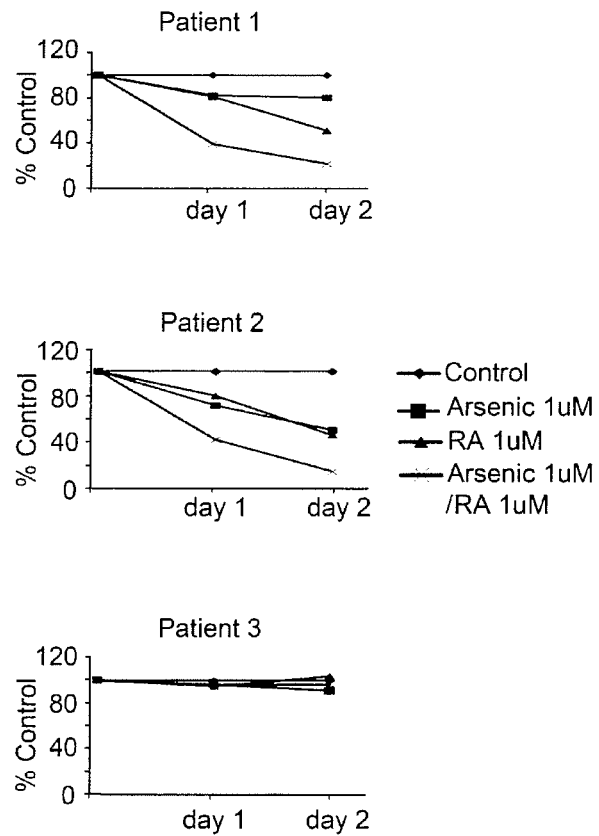

Primary leukemic cells derived from peripheral blood mononuclear cells or BM of three AML patients, were treated with RA and/or arsenic, as above. Patient 1 had APL with PML/RARA rearrangement, patient 2 harbored an NPM-1 mutation without Flt-3 ITD and patient 3 had AML-M6 with wt NPM-1. Cells from patients 1 and 2 were more sensitive to RA and arsenic treatment than those derived from patient 3 (FIG. 1D). Again, a strong synergy between RA and arsenic was observed, exclusively in patients 1 and 2 at any time point and dose (FIG. 1D and not shown). Collectively, RA and arsenic exert selective apoptosis on NPM-1 mutant AMLs ex vivo.

RA/Arsenic Reduce Marrow Blasts in NPM-1 Mutant AML Patients

Compassionate use of RA and arsenic was initiated in five previously untreated or relapsed elderly AML patients with normal karyotype and mutated NPM-1 that were judged unfit for chemotherapy. As expected from APL patients, this treatment was very well tolerated (22). BM blasts significantly decreased in three patients at day 15 post-treatment (FIG. 1E and not shown). BM blasts remained low while on therapy, but increased following its discontinuation (FIG. 1E). In patient 4, analysis of weekly BM aspirates, revealed that BM blasts increased initially from day 1 to day 15 of RA treatment (day 8 of RA/arsenic) (15% to 38%, respectively), and subsequently normalized at day 23 of RA treatment (day 16 of RA/arsenic) (5%), in a normo-cellular marrow. BM blasts remained low at day 39 while on therapy (6%), but re-increased at day 63 (33%), two weeks after therapy was discontinued (FIG. 1F). Importantly, throughout the treatment period, the patient became transfusion-independent. Thus, RA and arsenic exerted an in vivo antileukemic effect, with clearance of bone marrow blasts in this subset of AML patients.

Degradation of Mutant NPM-1 Drives RA/Arsenic-Induced Growth Inhibition

Figure 2A:
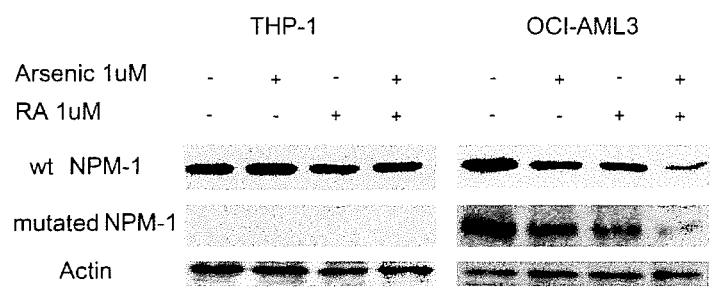
Figure 2B:
Figure 2C:
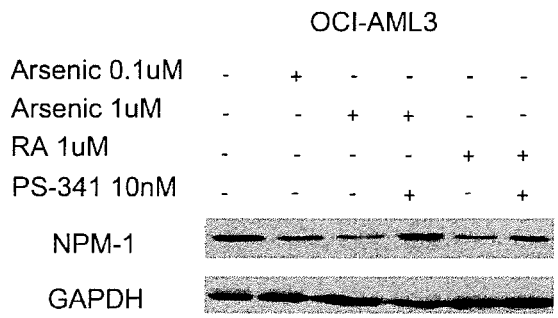
Figure 2D:
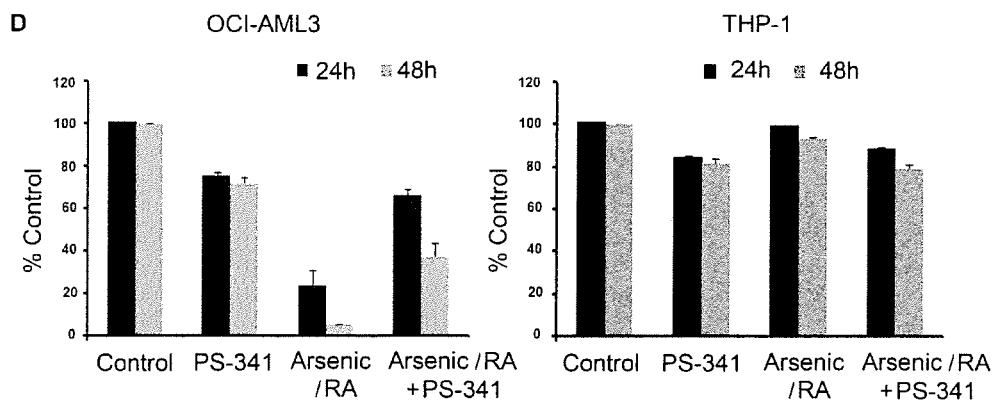

Because of the striking similarities between RA/arsenic effects on NPM-1 mutant AML cells and APL cells, we investigated the ability of this combination to induce degradation of the mutant NPM-1 oncoprotein. No effect of RA or arsenic on NPM-1 expression was observed in THP-1 and ML-2 cells (FIG. 2A and not shown). In contrast, RA or arsenic triggered NPM-1 degradation in OCI-AML3 cells, as assessed with an antibody detecting both wt and mutant proteins (FIG. 2A). Using an antibody selective for NPM-1 mutant protein, the amplitude of degradation was considerably higher. Collectively, this suggests that mutant NPM-1 is the primary target of RA and arsenic, and that the oligomerized, wt protein is co-degraded (FIG. 2A). Similar findings were observed in primary patient cells (FIG. 2B). Critically, both NPM-1 degradation and growth arrest were reversed following addition of the proteasome inhibitor PS-341 (FIGS. 2C and 2D) (CI 4.58 at 24 h). These results strongly suggest that RA/arsenic-induced growth arrest of AML cells with mutant NPM-1 is caused by proteasomal degradation of the mutated oncoprotein.

RA and Arsenic Restore the Normal Localization of both NPM-1 and PML

Figure 2E:
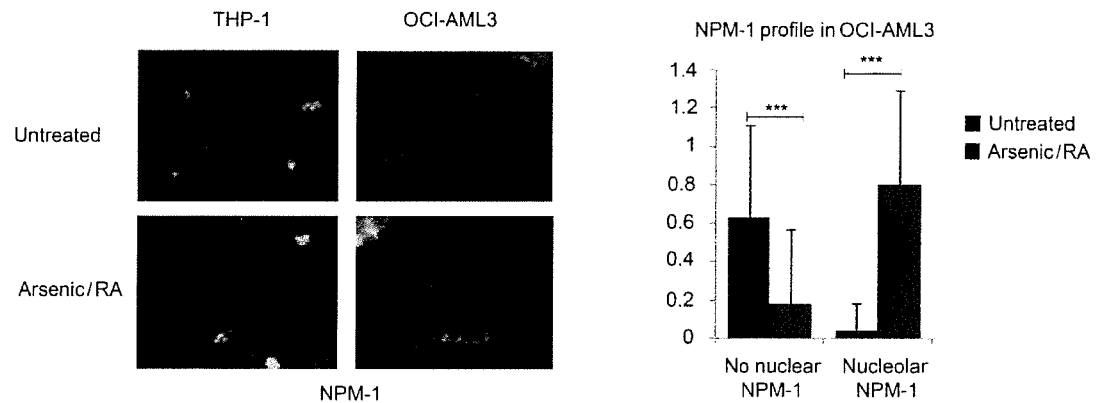

In NPM-1 mutant AMLs, NPM-1 is delocalized to the cytoplasm (FIG. 2E). Importantly, treatment with RA/arsenic restored the nucleolar localization of the remaining NPM-1 protein (FIG. 2E). This suggests that degradation of mutated NPM-1 triggered by RA/arsenic releases wt NPM-1 and thus corrects the defects in nucleolar organization. Remarkably, in vivo RA/arsenic treatment resulted in complete NPM-1 nucleolar relocalization in the blasts of one patient (FIG. 3A), although mutant NPM-1 was not fully degraded (data not shown). Thus, therapy rapidly corrects the defects in nucleolar organization (and presumably function) imposed by NPM-1 mutation.

Figure 3A:
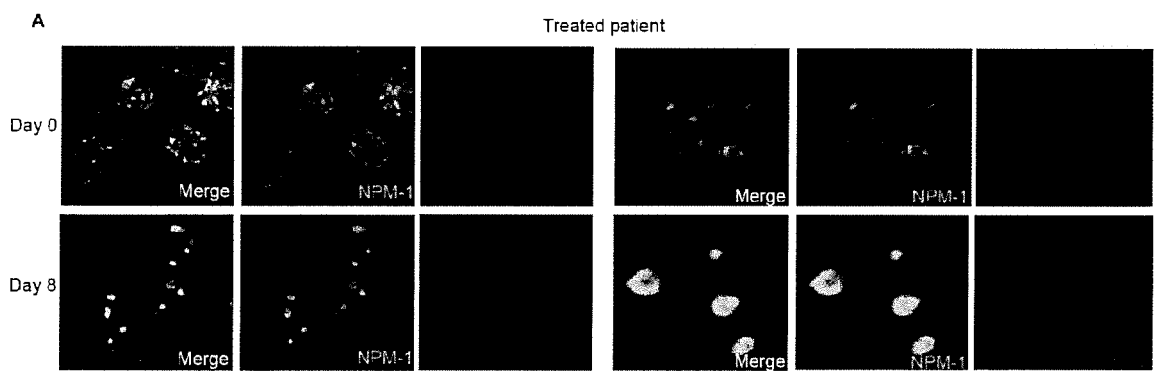
Figure 3B:
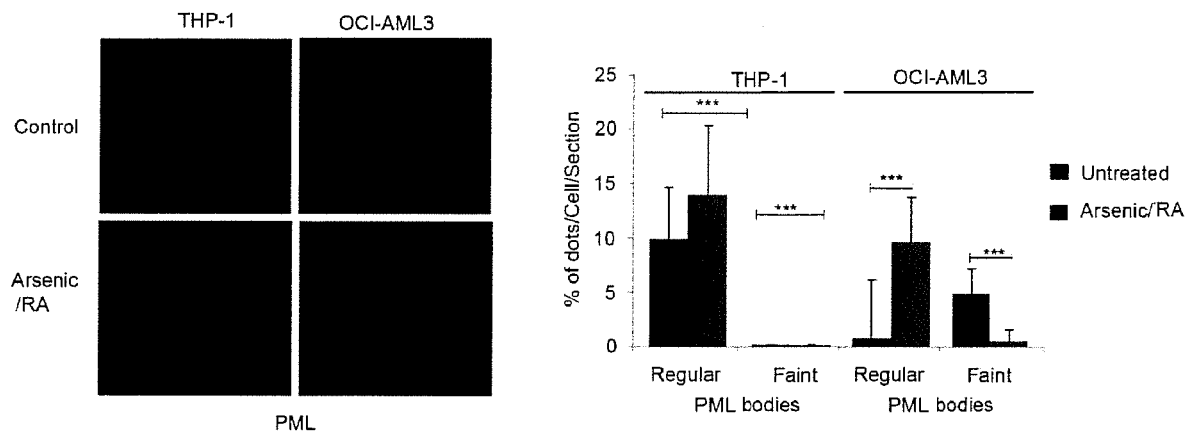
Figure 3C:
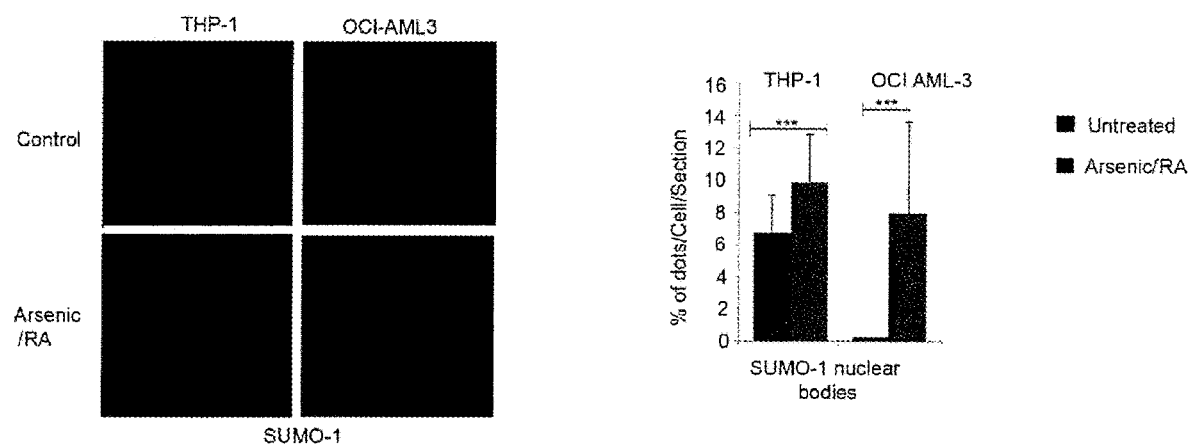

PML NBs constitute platforms for post-translational modifications, notably sumoylation, that have been repeatedly implicated in transformation. Yet, alterations in PML NBs were not previously described in NPM-1 mutant AMLs. Unexpectedly, in OCI-AML3 cells, PML NBs were significantly smaller and far less numerous than in THP-1 cells. The same conclusion was reached using SUMO-1 antibodies (FIG. 3B-C). Moreover, in NPM-1 mutated primary AML cells, we observed small PML NBs and a significant overlap between nuclear, but extra-nucleolar, NPM-1 and PML (FIG. 3A). As expected, treatment with RA/arsenic enhanced PML NB formation in both OCI-AML3 and THP-1 cells, however this effect was more pronounced in NPM-1 mutated cells and was accompanied by enhanced SUMO-1 NB formation in OCI-AML3 cells (FIG. 3B-C). These results demonstrate the disorganization of PML/SUMO-1 NBs in NPM-1 mutant AML, and could suggest that their restoration contributes to the therapeutic efficacy of RA/arsenic, as in APL (15, 23).

Discussion:

We and others have demonstrated that, in APL, PML/RARA degradation by arsenic or RA triggers differentiation and activates a P53 senescence checkpoint that culminates in APL eradication (13, 24-25). The two degradation pathways have been extensively characterized and reflect the direct binding of arsenic onto PML and of RA onto its receptor, RARA (26). Treatment-induced senescence was linked to the restoration of PML NBs previously disrupted by PML/RARA expression (15). The results obtained here with NPM-1 mutant AML bear unexpected similarities with APL. First, mutant NPM-1 is degraded upon RA or arsenic exposure. Second, mutant NPM-1 disorganizes PML bodies and RA/arsenic restores nuclear organization (nucleolar NPM-1 with normal PML/SUMO bodies) ex vivo and in vivo. Finally, BM blasts are significantly reduced in some treated patients. These AMLs are addicted to continuous expression of the mutant protein (27), so that degradation of mutant NPM-1 most likely triggers apoptosis. As in APL, reformation of PML bodies could also contribute to therapy response (15, 28). How RA or arsenic selectively target mutant NPM-1 protein remains obscure. PML NBs are SUMO-dependent degradation factories activated by interferons and oxidative stress (29). Arsenic dramatically enhances formation of PML NBs and promotes the degradation of some PML-associated proteins. That pre-treatment with interferon alpha significantly accelerated arsenic-induced degradation of mutant NPM-1 (data not shown) could suggest a role of PML and/or SUMOs in the degradation process. Moreover, altered PML NBs biogenesis in NPM-1 mutant AMLs could reflect a physical interaction between PML and mutant NPM-1, which is massively sumoylated (30). Other similarities between PML and NPM-1 exist, including sumoylation, link to P53 control, interferon signaling or oxidative stress (31). How RA promotes the selective degradation of mutant NPM-1 remains unclear, and future studies should investigate the catabolic pathways involved.

Because elderly AML patients with NPM-1 mutations are not eligible for treatment with chemotherapy, some patients were treated on a compassionate basis with the RA/arsenic combination used in APL. While we did not observe complete remissions, the leukemia clearly regressed in several patients. Strikingly, we could demonstrate the relocalization of NPM-1 to the nucleolus and reformation of PML bodies in primary AML blasts, demonstrating therapy-induced restoration of nuclear organization. Yet, we could not obtain complete degradation of mutant NPM-1 in AML patients in vivo. In APL, clinical response mirrors the extent of PML/RARA degradation and only full oncoprotein catabolism yields remissions (15, 17). Some in vivo/ex vivo differences may be responsible for this blunted in vivo response to the RA/arsenic combination. For example, the arsenic-induced oxidative stress required for full NPM-1 degradation may not be reached in patients. Pre-clinical optimization, for example using mouse models, should address this point.

These unexpected findings constitute a striking parallel to the RA/arsenic-mediated degradation of PML/RARA in APL. Our observations could explain the survival benefit of adding RA to chemotherapy in this subset of patients, and warrants clinical evaluation of the frontline RA/arsenic combination in elderly ones.

REFERENCES

Throughout this application, various references describe the state of the art to which this invention pertains. The disclosures of these references are hereby incorporated by reference into the present disclosure.

1. Ferrara F. Conventional chemotherapy or hypomethylating agents for older patients with acute myeloid leukaemia? *Hematol Oncol.* 2014; 32(1):1-9.

2. Grimwade D, Hills R K, Moorman A V, et al. Refinement of cytogenetic classification in acute myeloid leukemia: determination of prognostic significance of rare recurring chromosomal abnormalities among 5876 younger adult patients treated in the United Kingdom Medical Research Council trials. *Blood.* 2010; 116(3):354-65.

3. Frohling S, Schlenk R F, Breitruck J, et al. Prognostic significance of activating FLT3 mutations in younger adults (16 to 60 years) with acute myeloid leukemia and normal cytogenetics: a study of the AML Study Group Ulm. *Blood.* 2002; 100(13):4372-80.

4. Grisendi S, Bernardi R, Rossi M, et al. Role of nucleophosmin in embryonic development and tumorigenesis. *Nature.* 2005; 437(7055):147-53.

5. Falini B, Bolli N, Liso A, et al. Altered nucleophosmin transport in acute myeloid leukaemia with mutated NPM1: molecular basis and clinical implications. *Leukemia.* 2009; 23(10):1731-43.

6. Cheng K, Sportoletti P, I to K, et al. The cytoplasmic NPM mutant induces myeloproliferation in a transgenic mouse model. *Blood.* 2010; 115(16):3341-5.

7. Chou S H, Ko B S, Chiou J S, et al. A knock-in Npm1 mutation in mice results in myeloproliferation and implies a perturbation in hematopoietic microenvironment. *PLoS One.* 2012; 7(11):e49769.

8. Mallardo M, Caronno A, Pruneri G, et al. NPMc+ and FLT3 ITD mutations cooperate in inducing acute leukaemia in a novel mouse model. *Leukemia.* 2013; 27(11):2248-51.

9. Mupo A, Celani L, Dovey O, et al. A powerful molecular synergy between mutant Nucleophosmin and F1t3-ITD drives acute myeloid leukemia in mice. *Leukemia.* 2013; 27(9):1917-20.

10. Shlush L I, Zandi S, Mitchell A, et al. Identification of pre-leukaemic haematopoietic stem cells in acute leukaemia. *Nature.* 2014; 506(7488):328-33.

11. Vassiliou G S, Cooper J L, Rad R, et al. Mutant nucleophosmin and cooperating pathways drive leukemia initiation and progression in mice. *Nat Genet.* 2011; 43(5): 470-5.

12. Schlenk R F, Dohner K, Kneba M, et al. Gene mutations and response to treatment with all-trans retinoic acid in elderly patients with acute myeloid leukemia. Results from the AMLSG Trial AML HD98B. *Haematologica.* 2009; 94(1):54-60.

13. Dos Santos G A, Kats L, Pandolfi P P. Synergy against PML-RARa: targeting transcription, proteolysis, differentiation, and self-renewal in acute promyelocytic leukemia. *J Exp Med.* 2013; 210(13):2793-802.

14. de The H, Chen Z. Acute promyelocytic leukaemia: novel insights into the mechanisms of cure. *Nat Rev Cancer.* 2010; 10(11):775-83.

15. Ablain J, Rice K, Soilihi H, et al. Activation of a promyelocytic leukemia-tumor protein 53 axis underlies acute promyelocytic leukemia cure. *Nat Med.* 2014; 20(2): 167-74.

16. Lallemand-Breitenbach V, Guillemin M C, Janin A, et al. Retinoic acid and arsenic synergize to eradicate leukemic cells in a mouse model of acute promyelocytic leukemia. *J Exp Med.* 1999; 189(7):1043-52.

17. Nasr R, Guillemin M C, Ferhi O, et al. Eradication of acute promyelocytic leukemia-initiating cells through PML-RARA degradation. *Nat Med.* 2008; 14(12):1333-42.

18. Ravandi F, Estey E, Jones D, et al. Effective treatment of acute promyelocytic leukemia with all-trans-retinoic acid, arsenic trioxide, and gemtuzumab ozogamicin. *J Clin Oncol.* 2009; 27(4):504-10.

19. Shen Z X, Shi Z Z, Fang J, et al. All-trans retinoic acid/As2O3 combination yields a high quality remission and survival in newly diagnosed acute promyelocytic leukemia. *Proc Natl Acad Sci USA.* 2004; 101(15):5328-35.

20. Lo-Coco F, Avvisati G, Vignetti M, et al. Retinoic acid and arsenic trioxide for acute promyelocytic leukemia. *N Engl J Med.* 2013; 369(2): 111-21.

21. Chou T C. Drug combination studies and their synergy quantification using the Chou-Talalay method. *Cancer Res.* 2010; 70(2):440-6.

22. Efficace F, Mandelli F, Avvisati G, et al. Randomized Phase III Trial of Retinoic Acid and Arsenic Trioxide Versus Retinoic Acid and Chemotherapy in Patients With Acute Promyelocytic Leukemia: Health-Related Quality-of-Life Outcomes. *J Clin Oncol.* 2014.

23. Lehmann-Che J, Bally C, de The H. Resistance to therapy in acute promyelocytic leukemia. *N Engl J Med.* 2014; 371(12):1170-2.

24. Ablain J, Leiva M, Peres L, et al. Uncoupling RARA transcriptional activation and degradation clarifies the bases for APL response to therapies. *J Exp Med.* 2013; 210(4): 647-53.

25. Vitaliano-Prunier A, Halftermeyer J, Ablain J, et al. Clearance of PML/RARA-bound promoters suffice to initiate APL differentiation. *Blood.* 2014 (online)

26. Jeanne M, Lallemand-Breitenbach V, Ferhi O, et al. PML/RARA oxidation and arsenic binding initiate the antileukemia response of As2O3. *Cancer Cell.* 2010; 18(1):88-98.

27. Balusu R, Fiskus W, Rao R, et al. Targeting levels or oligomerization of nucleophosmin 1 induces differentiation and loss of survival of human AML cells with mutant NPM1. *Blood.* 2011; 118(11):3096-106.

28. Lallemand-Breitenbach V, de The H. PML nuclear bodies. *Cold Spring Harb Perspect Biol.* 2010; 2(5): a000661.

29. Sahin U, Lallemand-Breitenbach V, de The H. In Brief: PML Nuclear Bodies: Regulation, function and therapeutic perspectives. *J Pathol.* 2014.

30. Haindl M, Harasim T, Eick D, et al. The nucleolar SUMO-specific protease SENP3 reverses SUMO modification of nucleophosmin and is required for rRNA processing. *EMBO Rep.* 2008; 9(3):273-9.

31. Lindstrom M S. NPM1/B23: A Multifunctional Chaperone in Ribosome Biogenesis and Chromatin Remodeling. *Biochem Res Int.* 2011; 2011:195209.

The invention claimed is:

1. A method for reversing, alleviating, or inhibiting the progress of acute myeloid leukemia (AML) driven by mutation of the NPM-1 gene in a subject in need thereof comprising administering to the subject a therapeutically effective amount of at least one arsenic compound and a therapeutically effective amount of at least one retinoid, wherein the subject has a normal karyotype, wherein the therapeutically effective amount of the at least one arsenic compound provides a serum concentration of 0.1 µM to 1 µM, wherein the therapeutically effective amount of the at least one retinoid provides a serum concentration of 0.3 µM to 1 µM, wherein the subject is not receiving chemotherapy prior to said administering step, and wherein the at least one arsenic compound is arsenic trioxide ($As_2O_3$) and the at least one retinoid is a retinoic acid.

2. The method of claim 1, wherein the ratio of $As_2O_3$ to retinoic acid administered to the subject is from 1:1 to 1:3.

3. A method for reversing, alleviating, or inhibiting the progress of acute myeloid leukemia (AML) driven by mutation of the NPM-1 gene in a subject in need thereof comprising administering to the subject a therapeutically effective amount of at least one arsenic compound and a therapeutically effective amount of at least one retinoid, wherein the subject has a normal karyotype, wherein the therapeutically effective amount of the at least one arsenic compound provides a serum concentration of 0.1 µM to 1 µM, wherein the therapeutically effective amount of the at least one retinoid provides a serum concentration of 0.3 µM to 1 µM, wherein the at least one arsenic compound and the at least one retinoid are administered without any other chemotherapeutic agent, and wherein the at least one arsenic compound is arsenic trioxide ($As_2O_3$) and the at least one retinoid is a retinoic acid.

4. The method of claim 3, wherein the ratio of $As_2O_3$ to retinoic acid administered to the subject is from 1:1 to 1:3.

* * * * *